(12) United States Patent
Nelson et al.

(10) Patent No.: US 7,564,367 B2
(45) Date of Patent: Jul. 21, 2009

(54) AIRCRAFT DOOR DETECTOR/WARNING DEVICE

(75) Inventors: Barry Michael Nelson, Enumclaw, WA (US); Spencer Ray Nelson, Sumner, WA (US)

(73) Assignee: Airport Mechanical Services, Inc., Enumclaw, WA (US)

( * ) Notice: Subject to any disclaimer, the term of this patent is extended or adjusted under 35 U.S.C. 154(b) by 386 days.

(21) Appl. No.: 10/834,465

(22) Filed: Apr. 29, 2004

(65) Prior Publication Data

US 2005/0024222 A1      Feb. 3, 2005

(51) Int. Cl.
G08B 21/00      (2006.01)

(52) U.S. Cl. .............. 340/686.6; 340/686.1; 340/682.2; 14/69.5; 14/71.3; 14/71.5; 114/362

(58) Field of Classification Search .............. 340/686.1, 340/687, 682.2, 686.6; 14/69.5, 71.3, 71.5, 14/71.7; 114/362
See application file for complete search history.

(56) References Cited

U.S. PATENT DOCUMENTS

| | | | | |
|---|---|---|---|---|
| 5,105,495 A | * | 4/1992 | Larson et al. | 14/71.5 |
| 5,257,431 A | * | 11/1993 | Larson et al. | 14/71.5 |
| 5,950,266 A | * | 9/1999 | Streeter et al. | 14/69.5 |
| 6,496,996 B1 | * | 12/2002 | Worpenberg et al. | 14/71.5 |

OTHER PUBLICATIONS

TianDa Device, 1 page, the date of availability of this device is not known.
Apex Safety Shoe, 6 pages, the date of availability of this device is not known.
Declaration of Barry M. Nelson; Jul. 11, 2007; 3 pages.

* cited by examiner

*Primary Examiner*—Daryl C Pope
(74) *Attorney, Agent, or Firm*—Perkins Coie LLP (57) ABSTRACT

Disclosed is an electromechanical system for minimizing passenger door contact with the Passenger Loading Bridge (PLB) floor and subsequent damage to said door, during passenger loading or off loading. The system, as configured at the Cab entry, senses the proximity of the aircraft door by contacting a sensing pad, attached to the PLB floor. This initiates a sequence of events. 1) Both visual and auditory alarms are initiated to alert the passenger loading agents and/or the bridge operator of a fault. 2) The PLB is moved down and away from the door sufficiently to prevent the PLB floor from coming in contact with the door. The loading agents or PLB operator can then perform the necessary steps to reset the device and continue loading.

19 Claims, 5 Drawing Sheets

Operational View of Control Console and Panel

Figure 1
Cross Sectional View of Sensing Pad

Figure 2
Existing PLB Installation
As Currently Configured

Figure 3
PLB Installation With "Aircraft Door Detector/ Warning Device" In Place Figure 4
Operational View of Control
Console and Panel Figure 5
Schematic for "Aircraft Door Detector/Warning Device"
Note: Dashed boxes indicate device in Control Console

AIRCRAFT DOOR DETECTOR/WARNING DEVICE

FEDERALLY SPONSORED RESEARCH

Not Applicable

SEQUENCE LISTING OR PROGRAM

Not Applicable

BACKGROUND OF THE INVENTION

1. Field of Invention

This invention relates to passenger loading bridges, which are self leveling, and a means of preventing the loading bridge floor from contacting and damaging the aircraft door during passenger loading and unloading functions.

2. Prior Art

The Airlines have had a problem with aircraft passenger entrance door damage. The door damage occurs when the door makes contact with the Passenger Loading Bridge (PLB) floor while loading the aircraft. The PLB is equipped with an auto level device that is supposed to keep the floor at a set level in relation to the aircraft. As passengers are boarding or exciting the aircraft, the resulting change in weight causes the aircraft to elevate or lower. Bridge function before apparatus is installed: The existing apparatus has an operate circuit that lets you operate the Horizontal drive, (manually), Vertical drive (manually), Canopy in and out, Cab rotate right and left, Adjustable Cab Floor (ACF) floor up and down. In the Auto level circuit, the arm and wheel are extended out to the aircraft (manually) to detect the aircraft vertical (latitude) position relative to the PLB deck. In the off circuit all functions are cancelled. If the operator fails to set the auto level or if the auto level malfunctions, there is no redundant system to protect the door from making contact with the floor. If this Auto level does not function properly or is disengaged, there is nothing to keep the door from being damaged by contacting the PLB floor. If the PLB is turned off with the off button, all functions are cancelled. At this time, there is no indication the floor is making contact with the aircraft door until it is too late. Consequently, the door is distorted and repair or replacement is necessary. The cost for this service has been as high as $200,000. This is in addition to the time the aircraft is out of service and the time required unloading the aircraft and finding other flights for passengers. Other devices to detect door location have to be manually placed under the door and manually plugged into the wall and only have two functions. These are used with little success. In most cases the gate agent is not trained on where to place the device or where to plug it into the wall or since it is portable, it may not be available for use. Also the gate agent does not have time to figure out the procedure of such a device Objects and advantages: Our device is stationary and hard wired to the PLB controls needing no set up When activated, it sounds two audible alarms and displays one visual alarm. It retracts and resets the auto level arm automatically. It drives the PLB down away from the aircraft door. If the PLB is turned off with the off button, all functions will occur except for the vertical down alerting the agent that the aircraft door is too close to the PLB door. Our device performs all these functions regardless of which position the selector switch is in (auto level, off, operate). Our device monitors the integrity of the system 24/7. A visual alarm alerts the agent that there is a fault in the system. This device has been demonstrated for several safety personnel at a major International Airport. They expressed great enthusiasm about implementing this on all the PLBs in their system.

SUMMARY OF THE INVENTION

This device detects an aircraft door before it makes contact with the floor of a PLB. This detector senses a door when the door and PLB floor are within 1.25 inches of each other thus avoiding any contact and resulting damage. If the PLB is in Auto level when the door detector activates, the PLB will vertically drive down 3 inches (away from the door) to avoid door damage. The auto level wheel and arm will retract and reset. If the selector switch located on the control console is in the "Off" position, the door detector will still detect the door at the same distance as before—still driving the PLB down 3 inches. If the selector switch is in the "Operate" mode, the door detector will detect the door when it comes within 1.25 inches of the floor. This movement is the same as if the auto level was functioning properly and activating the vertical drive down 3 inches. The door detector, when activated, will set off warning functions simultaneously: an audible signal for 4 seconds, a strobe on the PLB deck, an audible signal at the terminal (continuous until reset by "Power On" button at the PLB control console), the vertical drive down contactor, which runs the PLB down through a set of contacts and motor or motors, and the retract and extend actuator for the auto level. If the hi-voltage power has been turned off by the "Off" button on the control console, all alarms and auto level operations will operate accordingly. The PLB will not move vertically down away from the aircraft door. This device is unique. The device configuration is independent of the type or model of aircraft. There is no requirement for the sensing device to be manually placed under the door for each operation or an electrical connection to be made. This detection device is hardwired to the controls of the PLB. After being activated, it performs several functions automatically, adjusting the PLB level ensuring the door is out of harm's way. If the operator changes the level of the ACF floor, and inadvertently raises the floor closer to the door. There is no redundant system to keep the door from making contact with the floor. If the operator swings the door open to greet passengers, and the door is less than 2" from the floor, there is no protection to keep the door from making contact with the floor. (The auto level needs an 1½" of movement before it will make an elevation correction). The canopy function is not critical.

Figure 5:
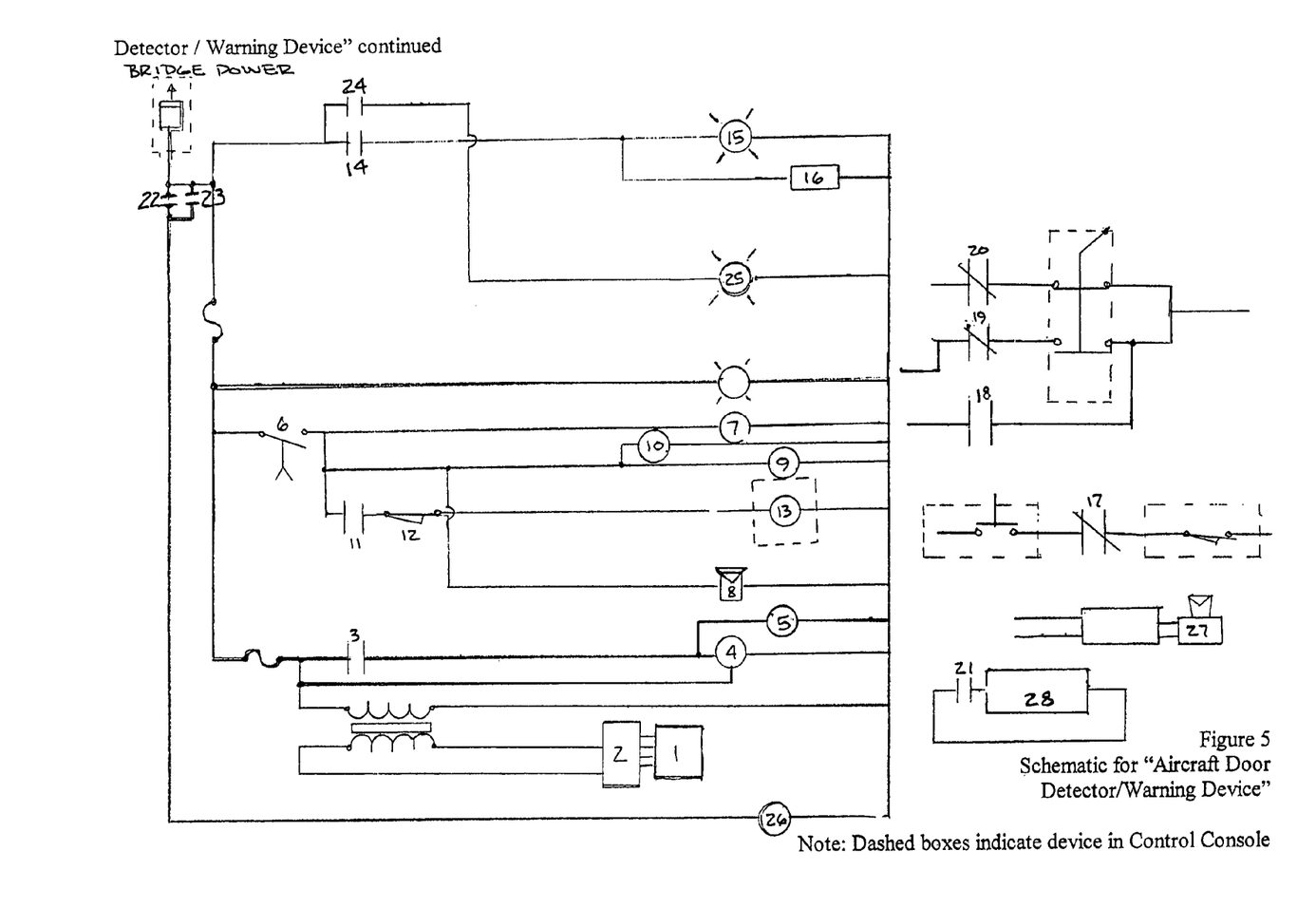
FIG. 5 Schematics (See following page)

1 The sensing pad is depressed more than ½" sending a signal to 2 the control module (which is constantly monitoring the integrity of the sensing pad) which closes a set of contacts 3 initiating 4 TDR and 5 TDR 2 and energizing an audible alarm 4 TDR times out and 6 contacts close activating 7 LR1 and 10 VDC and 9 ALR and closing 11 a set of contacts passing through a set of contacts 12 and activating 13 down contactor 9 ALR switches contacts 18, 19, 20 20 opens interrupting power to the auto level motor extend 19 opens interrupting power to the auto level retract 18 closes letting power from 6 energize the auto level motor to retract after 4 TDR has timed out contacts 11, 18, 19, 20 change back to their original state 10 VDC opens 17 contact 7 LR1 is energized closing contacts 14 energizing a red strobe light and advances a counter 7 LR1 stays latched until 22 or 23 reset buttons are depressed closing the contacts energizing LR2 opening 14 contact and 21 contact this operation puts all circuits back to their normal state if the sensing pad is depressed for more than 5 seconds 5 TDR2 is able to time out and 24 contact is closed energizing an amber light indicating a fault in the system or something is setting on the sensing pad. When 23 power on reset is closed the LR unlatch opens causing the Issacs transmitter to send a message to the remote 12 volt buzzer 27 silencing the buzzer.

DETAILED DESCRIPTION—PREFERRED EMBODIMENT

Figure 1:
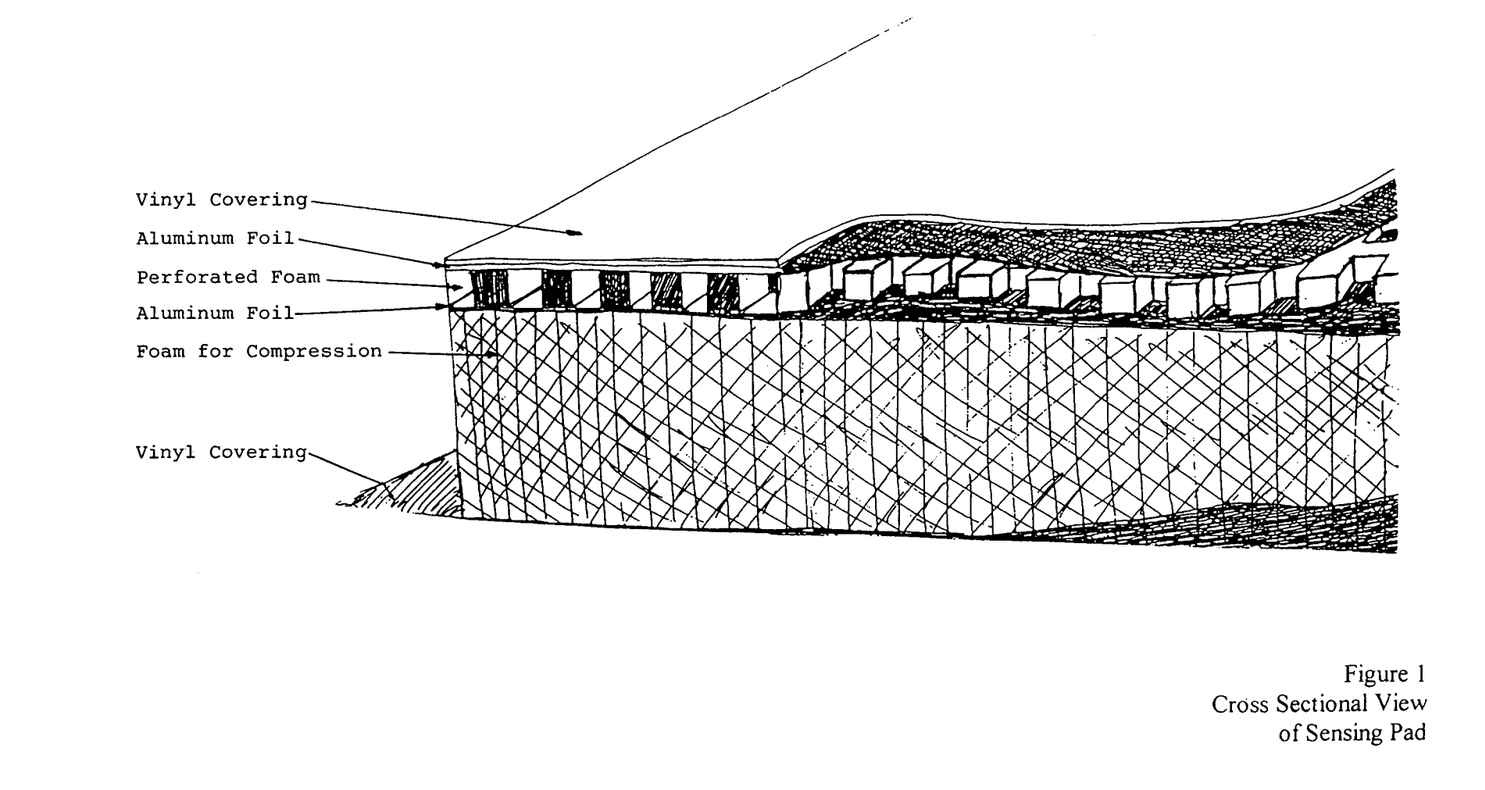
FIG. 1 Cross section view of sensing pad
Figure 2:
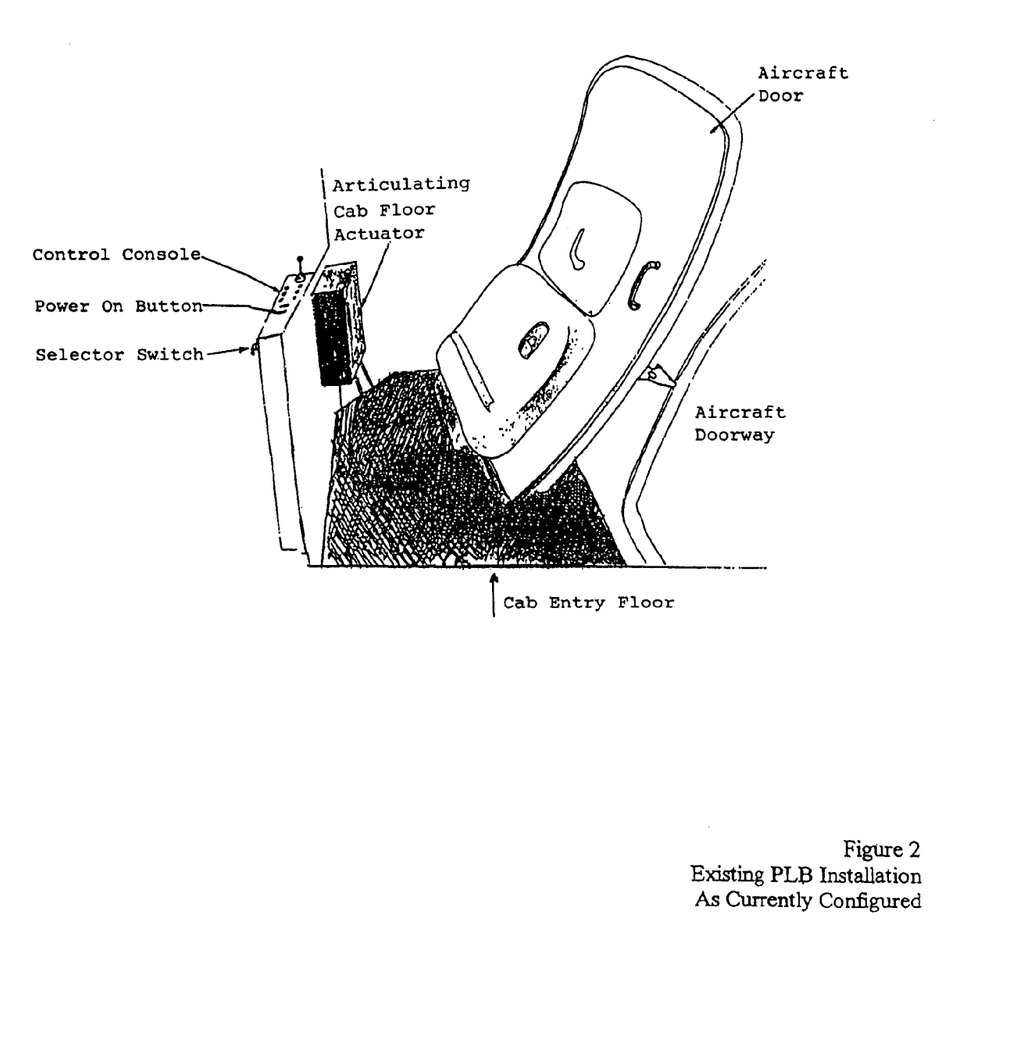
FIG. 2 Existing PLB installation as currently configured
Figure 3:
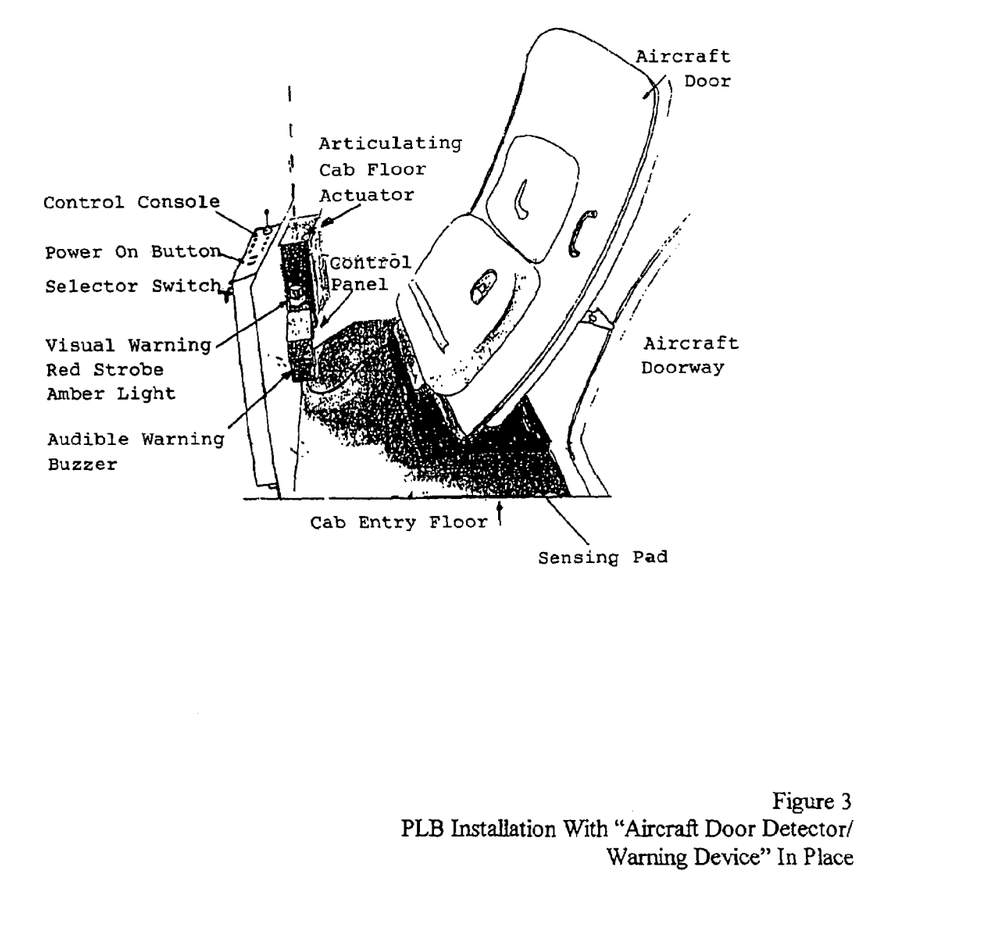
FIG. 3 PLB installation with Aircraft Door Detector/Warning Device in place
Figure 4:
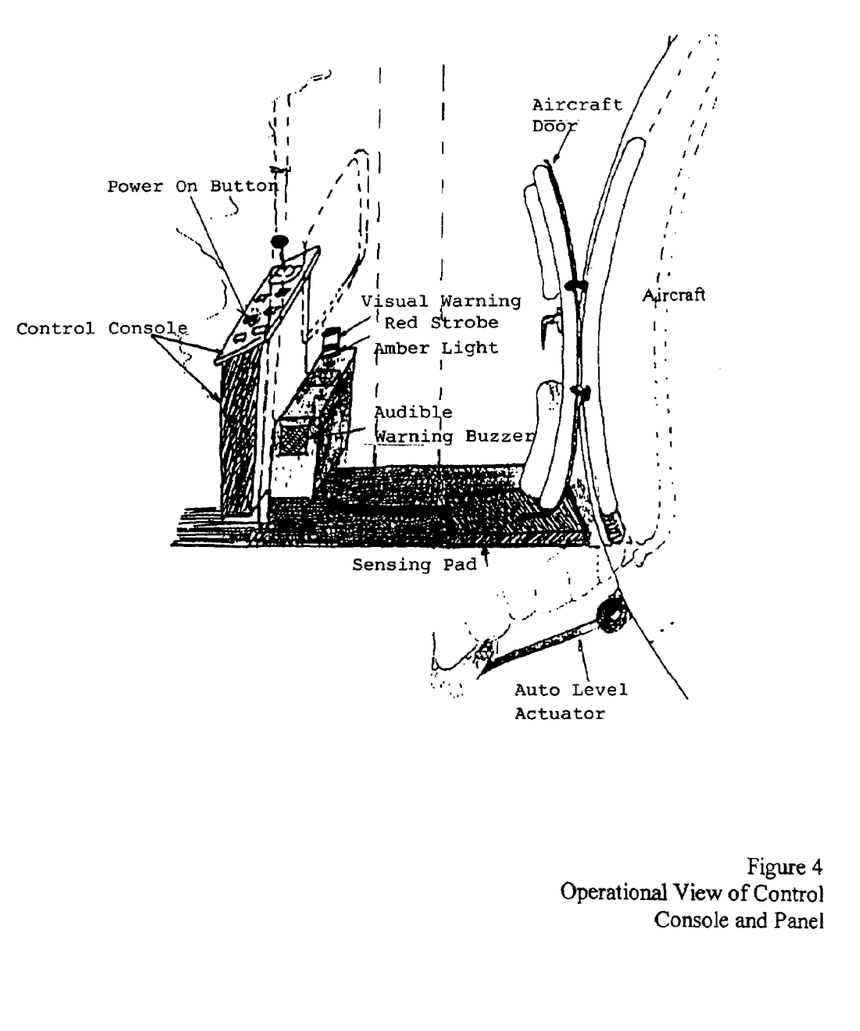
FIG. 4 Operational view of Control Console and Panel

Electro-mechanical motion sensing: The preferred embodiment uses a 22"×36"×2" vinyl enclosed open cell foam insert with two aluminum foil sheets separated by a piece of perforated foam. When the sensing device is compressed ½", the foil sheets touch each other completing an electrical circuit. Refer to FIG. 1 for a cross-sectional view of the sensing device. Another method is a limit switch that lies on its side. A flexible rod or arm extends beyond the switch staying parallel with the switch. When the flexible rod or arm is deflected, a set of contacts in the switch close completing an electrical circuit. One more method is a laser beam. While activated, anything interrupting the beam will cause a set of contacts to close completing an electrical circuit.

Positive stops: This device will stop after performing one cycle (determined by bridge type). Existing bridge limits are not affected. If the bridge down limits (solid state or mechanical) are activated, this device will not override the vertical limits.

Automatic reset: After actuation of the sensing device, the floor lowers away from the door. The auto level arm (if in the auto level selection) will retract automatically and extend automatically, resting against the aircraft fuselage. If the sensing device is activated for a duration longer than 6 seconds, a second relay is activated, automatically putting the unit into a fault mode. This fault will activate a visual warning device, to advise gate agents that there is a problem. Once the fault is removed, the system is automatically placed into a ready mode.

Redundant warning system: When this system is actuated a buzzer sounds for approximately 4 seconds, a strobe light illuminates until the system has been manually reset, and a second buzzer at the rotunda sounds until the system has been manually reset.

Operator training: After each installation a training session will be held for all gate agents and operator personnel. This will acquaint the operators with unique situations answering any procedural questions, the "what ifs" and the "how tos".

Placement of sensing device: The sensing pad or sensing device needs to be positioned so that the door or object being protected is directly above it. This is why a pad is used in this application. It covers a large area sensing the door at any angle from 90 degrees to 180 degrees without being repositioned for every flight.

Method of attachment: The sensing device may be attached to the PLB floor by various ways. One method is Velcro® hook and loop fastened to the sensing edge and to the floor. This would make it any easy removal for replacement or aircraft maintenance. Attachment around the perimeter of the sensor via screws is not recommended for fear of damage to a heating element in the floor if equipped. The method currently used is to screw down the 1" flap that forms the perimeter of the sensing device to a steel member that spans the width of the cab entry.

Not aircraft specific: This device will adapt to any aircraft, any door opening. Boeing 707, 720, 727, 737, 747, 757, 777, 717, DC 9, MD 80, MD 90 series, Airbus 318, 319, 320, 340, CRJ, ERJ, IL series, and TU series.

Not bridge specific: This device can be fitted to any loading bridge style or make, as long as there is a hard surface under the sensing device. This device can be installed on any loading bridge either presently manufactured or designs that are no longer manufactured, including designs of fixed, apron, radial, elevated, electric over hydraulic, electric over mechanical.

Operation not dependent on selector switch mode: All PLBs have some type of selector switch to give the operator a choice of functions for bridge operation. Most have auto level off, and operate. This device will function properly in any of these modes. The auto level circuit is intended to keep the floor or the passenger loading bridge and the aircraft passenger door threshold at the same relative position to each other during loading and unloading or fueling. The off circuit shuts down all motion circuits: Vertical drive, Horizontal drive, Canopy in and out, Cab rotate, Auto level, ACF floor.

No alterations are necessary to existing apparatus: The installation of this device does not make it necessary to revise any structural members or eliminate any fire barriers.

Does not interfere with existing operation: This device is independent of the existing PLB or apparatus and its electrical circuitry. If this unit becomes defective in any way, the PLB or apparatus will function normally.

Function is independent of floor slope: This device will work whether the slope of the bridge or floor is negative or positive off the horizontal place.

Operation

The door detector is a device, which keeps the aircraft door from making contact with the floor of a Passenger Loading Bridge (PLB). This device is not something that has to be placed under the door of each individual flight or plugged in. The door detector is hardwired to the controls of the loading bridge. If the door compresses the sensing surface to within 1.25" of the existing floor, a series of events will take place. The bridge vertical drive will be activated in the down direction for 4 seconds moving the floor away from the door. At the same time an audible warning signal or buzzer sounds for 4 seconds. A strobe will illuminate and an audible signal or buzzer sounds at the terminal. These two devices will stay on until a gate agent cancels them by pushing the "power on" button at the control console on the PLB. If the selector switch at the control console is in the auto level mode while the bridge is lowering itself, the auto level wheel and arm will retract and reset against the aircraft. If the selector switch is on the "off mode", the bridge will lower, the buzzers will sound, and the strobe will illuminate until the gate agent cancels them by pushing the "power on" button. At that time, the gate agent should set the auto level. If the selector switch is in the "operate mode", all the functions just described will occur. If for any reason the door detector goes into a fault situation, there are indicator lights to alert the gate agent so that a technician can be contacted for immediate repair. This device is Electrical Testing Laboratory (ETL) listed. The cost of repairing or replacing a L1 door, flight delays, safety, security, and the cost and emotional considerations of off-loading passengers and making arrangements for other flights will be a thing of the past.

The invention claimed is:

1. A system for enabling passengers to enter and/or egress an aircraft, the system comprising:
   a passenger loading bridge including a section configured to be positioned proximate to a door of an aircraft and controls for moving the section, the section having an interior surface; and
   an assembly including a door detecting device positioned at the interior surface and a controller operably coupled to the door detecting device and the controls;
   wherein the controller is configured to operate the controls to move the section when the door activates the door detecting device;
   wherein the controls comprise a control console with at least on and off positions; and
   wherein the controller is configured to operate the controls independent of the position of the control console.

2. The system of claim 1 wherein:
   the door detecting device comprises a pressure-sensitive pad;
   the section comprises a floor;
   the pressure-sensitive pad is fixedly attached to the floor;
   the controller is configured to operate the controls to move the section downward when the door contacts the pressure-sensitive pad; and
   at least a portion of the pressure-sensitive pad is positioned on the section to be at least partially between the floor and an open aircraft door.

3. The system of claim 1 wherein the door detecting device comprises a pressure-sensitive pad.

4. The system of claim 1 wherein the door detecting device is attached to the interior surface.

5. The system of claim 1 wherein:
   the section comprises a floor; and
   the door detecting device is fixedly attached to the floor.

6. The system of claim 1 wherein:
   the section comprises a floor; and
   at least a portion of the door detecting device is positioned on the section to be at least partially between the floor and an open aircraft door.

7. The system of claim 1 wherein the controller is configured to operate the controls to move the section downward when the door contacts the door detecting device.

8. An assembly for detecting a door of an aircraft at a passenger loading bridge, the assembly comprising:
   a pressure-sensitive pad for sensing the door of the aircraft, the pad being configured for placement in the passenger loading bridge; and
   a controller operably coupled to the pad, the controller being configured to be hardwired to the passenger loading bridge to operate the passenger loading bridge when the pressure-sensitive pad detects the door.

9. The assembly of claim 8 wherein the pressure-sensitive pad is sized to sense the door before the door contacts the passenger loading bridge when the door is open between approximately 90 degrees and approximately 180 degrees.

10. The assembly of claim 8 wherein the pressure-sensitive pad comprises:
    first and second generally planar conductive elements; and
    a deformable, insulative planar element positioned between the first and second conductive elements.

11. The assembly of claim 8 wherein the controller is configured to move the passenger loading bridge downward when the door contacts the pressure-sensitive pad.

12. The assembly of claim 8 wherein the pressure-sensitive pad is configured to be attached to a floor of the passenger loading bridge.

13. A method for installing an aircraft door detecting assembly to a passenger loading bridge, the method comprising:
    fixedly attaching a door detecting assembly to the passenger loading bridge with at least a portion of the door detecting assembly positioned to be at least partially between a floor of the passenger loading bridge and an open aircraft door; and
    electrically coupling the door detecting assembly to the passenger loading bridge with the door detecting assembly configured to operate the passenger loading bridge when an open aircraft door contacts the door detecting assembly.

14. The method of claim 13 wherein fixedly attaching the door detecting assembly comprises coupling the door detecting assembly to the passenger loading bridge such that the assembly is not moved and reattached to the bridge for an aircraft with a different configuration.

15. The method of claim 13 wherein fixedly attaching the door detecting assembly comprises coupling a pressure-sensitive pad to the passenger loading bridge.

16. The method of claim 13 wherein fixedly attaching the door detecting assembly comprises coupling the door detecting assembly to the floor of the passenger loading bridge.

17. The method of claim 13 wherein fixedly attaching the door detecting assembly comprises coupling a pressure-sensitive pad sized to detect the door before the door contacts the passenger loading bridge when the door is open between approximately 90 degrees and approximately 180 degrees.

18. The method of claim 13 wherein electrically coupling the door detecting assembly to the passenger loading bridge comprises operably connecting a controller of the door detecting assembly to controls of the passenger loading bridge.

19. The method of claim 13 wherein the door detecting assembly is configured to move at least a portion of the passenger loading bridge downward when the open aircraft door contacts the door detecting assembly.

* * * * *

UNITED STATES PATENT AND TRADEMARK OFFICE
CERTIFICATE OF CORRECTION

| | |
|---|---|
| PATENT NO. | : 7,564,367 B2 |
| APPLICATION NO. | : 10/834465 |
| DATED | : July 21, 2009 |
| INVENTOR(S) | : Nelson et al. |

It is certified that error appears in the above-identified patent and that said Letters Patent is hereby corrected as shown below:

On Drawing sheet 5 of 5, in Figure 5, line 1, above "BRIDGE POWER" delete "Detector / Warning Device" continued".

In column 1, line 55, after "device" insert -- . --.

In column 2, line 50, after "pad" insert -- . --.

In column 2, line 51, after "configured" insert -- . --.

In column 2, line 53, after "place" insert -- . --.

In column 2, line 54, after "Panel" insert -- . --.

In column 2, line 55, after "page)" insert -- . --.

In column 2, line 56, below "FIG. 5 Schematics (See following page)" insert -- Aircraft Door Detector/Warning Device Sequence of operation: --.

In column 3, line 10, delete "Issacs" and insert -- Isaacs --, therefor.

In column 4, line 17, after "level" insert -- , --.

In column 4, line 67, below "thing of the past." insert
-- Inasmuch as the foregoing specification comprises preferred embodiments of the invention, it is understood that various iterations, variations and modifications can be made herein in accordance with the inventive principles disclosed, without departing from the scope of the invention.

Signed and Sealed this
Twenty-eighth Day of August, 2012

David J. Kappos
*Director of the United States Patent and Trademark Office*

From the above it can be seen that the instant invention provides a highly responsive yet relatively simple means of preventing contact of the PLB floor with the passenger door and precluding any damage to said door.

Although a preferred embodiment of the instant invention has been illustrated and described, it will be apparent to those skilled in the art that various modifications may be made without departing from the spirit and scope of the present invention. --.